United States Patent [19]

Fahmy

[11] Patent Number: 4,686,209
[45] Date of Patent: Aug. 11, 1987

[54] CERTAIN N-(SUBSTITUTED-AMINOSULFINYL)-PHOSPHONAMIDOTHIOATE AND DITHIOATE PESTICIDES

[75] Inventor: Mohamed A. H. Fahmy, Modesto, Calif.

[73] Assignee: E. I. Du Pont de Nemours and Company, Wilmington, Del.

[21] Appl. No.: 817,633

[22] Filed: Jan. 10, 1986

[51] Int. Cl.$^4$ .......................... A01N 57/04; C07F 9/44
[52] U.S. Cl. ................................... 514/116; 558/171; 558/172; 558/173
[58] Field of Search ....................... 558/171, 173, 172; 514/116

[56] References Cited

U.S. PATENT DOCUMENTS 4,234,521  11/1980  Nelson .............................. 558/171
4,387,061   6/1983  Suzuki et al. ...................... 558/171

Primary Examiner—Anton H. Sutto

[57] ABSTRACT

Compounds of the formula

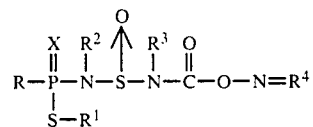

wherein the symbols have assigned meanings, and their use for controlling insects and mites.

7 Claims, No Drawings

CERTAIN N-(SUBSTITUTED-AMINOSULFINYL)PHOSPHONAMIDOTHIOATE AND DITHIOATE PESTICIDES

DESCRIPTION OF THE INVENTION

It has been found that insecticidal and acaricidal activity is possessed by compounds of the formula

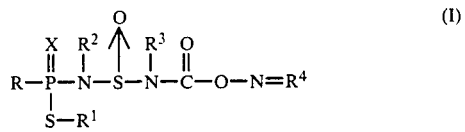

wherein R and $R^1$ each is alkyl or alkenyl of up to six carbon atoms, phenyl or benzyl; $R^2$ is alkyl, alkenyl or alkynyl of up to six carbon atoms, such alkyl substituted by phenyl; phenyl or phenyl substituted by one to three substituents selected from alkyl of one to six carbon atoms and halogen; $R^3$ is methyl; X is oxygen or sulfur; and $R^4$ is one of the moieties

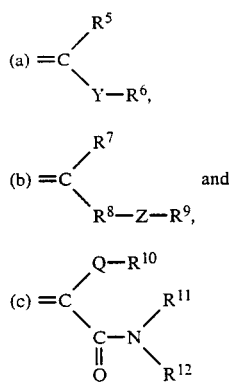

wherein $R^5$ is alkyl of one to five carbon atoms, Y is oxygen or sulfur, $R^6$ is alkyl of one to six carbon atoms, $R^7$ is hydrogen or alkyl of one to six carbon atoms, $R^8$ is methylene optionally substituted by one or two alkyl groups of one to two carbon atoms each, Z is —S—, —SO— or —SO$_2$—, $R^9$ is alkyl of one to four carbon atoms, Q is oxygen or sulfur, $R^{10}$ is alkyl of one to six carbon atoms, and $R^{11}$ and $R^{12}$ each is hydrogen or alkyl of one to four carbon atoms.

In these compounds, each alkyl moiety can be straight-chain or branched-chain. Preferably each of $R^2$, $R^3$, $R^5$, $R^6$, $R^9$, $R^{10}$, $R^{11}$, and $R^{12}$ is methyl; $R^7$ is hydrogen, methyl or 1-methylethyl, Y is sulfur, $R^8$ is —CHCH$_3$— or —C(CH$_3$)$_2$—, Z is —S— or —SO$_2$—, Q is sulfur and both $R^{11}$ and $R^{12}$ are methyl.

In these compounds, the phosphorus atom and the starred sulfur atom are chiral centers, and the compounds thus can exist in two diastereomeric forms (as used herein, the term diastereomer refers to a pair of enantiomers that is non-enantiomeric with the other pair of enantiomers). Later herein, in cases where the two forms have been separated, they will be referred to as "Isomer A" and "Isomer B", inasmuch as their absolute configuration has not been determined. Also, where a branched-chain alkyl moiety is present, a further chiral center will be present. Further, since these compounds also contain an oxime structural element, they also may exist in the form of geometrical isomers, referring to the spatial relationship of the moieties about the oxime double bond. In the cases of the compounds of this subclass whose preparation and isolation are described in the working examples, hereinafter, the geometric form(s) of the products has not been determined, and no attempt has been made to resolve the geometrically isomeric compounds involved. The activities of the isomers—optical and geometric,—with respect to insects may differ. This invention contemplates all active isomers, and mixtures thereof, whether resulting from the manner of preparation or deliberately formed.

The preparation and isolation of particular individual species of the genus of Formula I, are described in the Examples, hereinafter. Other typical individual species are the following, each identified in terms of the symbols of Formula I, subgenus (a) in all cases, R=ethyl, $R^3$=methyl, $R^5$=methyl, Y=S and $R^6$=methyl.

| Species | $R_1$ | $R_2$ |
|---------|-------|-------|
| A | propyl | methyl |
| B | propyl | ethyl |
| C | 1-methylpropyl | methyl |
| D | 1-methylpropyl | ethyl |
| E | 1,1-dimethylethyl | ethyl |
| F | 1-methylpropyl | 2-propynyl |
| G | 1-methylpropyl | benzyl |
| H | propyl | 2-propynyl |
| I | propyl | benzyl |

A compound of Formula I can be prepared by treating a compound of the formula

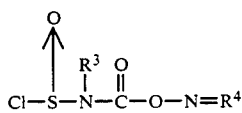

with a phosphonamidothioate or dithioate of the formula

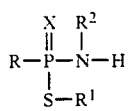

in the presence of a nitrogen base, such as pyridine, and in the presence of a solvent such as tetrahydrofuran. The treatment is carried out by adding the nitrogen base, then adding a solution of the compound of Formula II to a stirred solution of the compound of Formula III in the same solvent at a low temperature, for example about 0°–5° C., then warming the mixture to room temperature and stirring it until the reaction is complete. Moisture should be excluded from the reaction mixture.

A compound of Formula II can be prepared by treating a compound of the formula

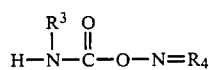

with thionyl chloride in the presence of a nitrogen base, such as pyridine, and in the presence of a solvent, tetrahydrofuran being suitable. The treatment is carried out by adding the nitrogen base to a stirred solution of the compound of Formula IV, then adding the sulfuryl chloride, which may be in solution in the solvent. The addition of the reagents is made at a low temperature—e.g., 0° C.-5° C.—then the mixture is warmed to complete the reaction. Moisture should be excluded from the reaction mixture.

The compounds of Formula IV are known in the art, being shown in U.S. Pat. Nos. 3,576,834; 3,217,037; 3,816,532; 3,658,870 and 3,875,232. Similarly, compounds of Formula II are known in the art: M. A. H. Fahmy and T. R. Fukuto, Journal of Agricultural and Food Chemistry, 1981, Volume 29, pages 567-572.

As is shown in U.S. Pat. No. 4,390,529, the phosphonamidodithioate precursors (III, S is sulfur) can be prepared by treating the appropriate phosphonodithioic chloride of the formula

(V)

with the appropriate primary amine $R^2-NH_2$        (VI)

The treatment may be conducted by adding a solution of the amine in a suitable solvent, such as water or acetone, to a solution of the chloride in a suitable solvent, such as acetone, at a low temperature (e.g., 5°-10° C.), then allowing the mixture to come to room temperature—or warming it if necessary—and holding it at that temperature until the reaction is complete.

As also is shown in U.S. Pat. No. 4,390,529, and in U.S. Pat. No. 4,190,652, the chloride precursor can be prepared by treating a phosphonic dichloride of the formula

(VII)

with the appropriate thiol, $R^1$—SH, in the presence of a solvent and an amine base, as hydrogen halide acceptor. Aromatic hydrocarbons, such as toluene, are suitable as the solvent. Any tertiary amine base is suitable, but the trialkylamines appear to be most suitable. Water should be excluded from the reaction mixture—as by using anhydrous reagents and conducting the treatment under nitrogen. Isolation of the product is effected by conventional techniques.

The phosphonamidothioate (III, X is oxygen) precursors can be prepared by treating the appropriate phosphonothioic chloride of the formula

(VIII)

with the appropriate primary amine $R^2-NH_2$        (IX)

The treatment may be conducted by adding a solution of the amine in a suitable solvent, such as acetone, to a solution of the chloride in a suitable solvent, such as acetone, at a low temperature (e.g., 5°-10° C.), then allowing the mixture to warm to room temperature—or warming it if necessary—and holding it at that temperature until the reaction is complete. It has been found that a higher yield of the desired product generally is obtained if water is excluded from the reaction system.

The phosphonothioic chloride precursor VIII also can be prepared by a method analogous to that described in U.S. Pat. No. 4,390,529 for preparing the corresponding phosphonamidothioic chloride—i.e., by treating a phosphonic dichloride of the formula

(X)

with the appropriate thiol, $R^1$ SH, in the presence of a solvent and an amine base, as hydrogen chloride acceptor. Aromatic hydrocarbons, such as toluene, are suitable as the solvent. Any tertiary amine base is suitable, but the trialkylamines appear to be most suitable. Water should be excluded from the reaction mixture—as by using anhydrous reagents and conducting the treatment under nitrogen.

The phosphonothioic chloride of Formula VIII also can be prepared by the method described by A. A. Neimysheva, et al., Journal of General Chemistry, U.S.S.R. (English), 1966, volume 36, pages 520-525—i.e., by slowly adding the appropriate sulfenyl chloride $R^1-S-Cl$        (XI)

to a stirred solution of the appropriate phosphonous dichloride of the formula

(XII)

in sulfur dioxide at a low temperature—e.g., −15° C. to −60° C.—then warming the resulting mixture to room temperature, stripping it of volatiles and vacuum distilling the residue to give the product.

The preparation and isolation of particular individual species of subgenus (a), Formula I, is described in the Examples, hereinafter other typical individual species of subgenera (b) and (c) are as follows, each being identified in terms of the symbols of Formula I.

Subgenus (b), R=ethyl, $R^2$=methyl, $R^3$=methyl, $R^9$=methyl:

| Species | $R^1$ | $R^7$ | $R^8$ | Z | X |
|---|---|---|---|---|---|
| A | 1-methylpropyl | H | —C(CH$_3$)$_2$— | S | O |
| B | 1-methylpropyl | H | —C(CH$_3$)$_2$— | S | S |
| C | 1-methylpropyl | H | —C(CH$_3$)$_2$— | —SO$_2$— | O |
| D | 1-methylpropyl | H | —C(CH$_3$)$_2$— | —SO$_2$— | S |
| E | 1,1-dimethylethyl | H | —C(CH$_3$)$_2$— | —S— | O |
| F | 1,1-dimethylethyl | H | —C(CH$_3$)$_2$— | —S— | S |
| G | 1,1-dimethylethyl | H | —C(CH$_3$)$_2$— | —SO$_2$— | O |
| H | propyl | H | —C(CH$_3$)$_2$— | —S— | O |
| I | propyl | H | —C(CH$_3$)$_2$— | —S— | S |
| J | 1-methylpropyl | methyl | —CHCH$_3$— | —S— | O |
| K | 1-methylpropyl | methyl | —CHCH$_3$— | —S— | S |
| L | 1-methylpropyl | methyl | —CHCH$_3$— | —SO$_2$— | O |
| M | 1-methylpropyl | methyl | —CHCH$_3$— | —SO$_2$— | O |
| N | 1-methylpropyl | 1-methylethyl | —CH$_2$— | —S— | O |

-continued

| Species | $R^1$ | $R^7$ | $R^8$ | Z | X |
| --- | --- | --- | --- | --- | --- |
| O | 1-methylpropyl | 1-methyl-ethyl | —CH$_2$— | —S— | S |
| P | propyl | 1-methyl-ethyl | —CH$_2$— | —S— | O |
| Q | propyl | 1-methyl-ethyl | —CH$_2$— | —S— | S |

Subgenus (c), R=ethyl, $R^2$=methyl, $R^3$=methyl, $R^{10}$=methyl, $R^{11}$=methyl, $R^{12}$=methyl:

| Species | $R^1$ | Q | X |
| --- | --- | --- | --- |
| R | 1-methylpropyl | S | O |
| S | 1-methylpropyl | S | S |
| T | 1,1-dimethylethyl | S | O |
| U | 1,1-dimethylethyl | S | S |
| V | propyl | S | O |
| W | propyl | S | S |

The preparation, isolation and testing of individual species of the genus of Formula I, in particular instances, are described in the following examples. In each case, the identity of each of the products, and each of the precursors, was confirmed as necessary by appropriate chemical and spectral analyses.

In Examples 1 through 8 following, each of the products was an individual species of subgenus (a) of Formula I, wherein X=oxygen, $R^2$=methyl, $R^5$=methyl, Y=sulfur and $R^6$=methyl, the identities of R, $R^1$ and $R^2$ being specified in the title of each example.

EXAMPLE 1

Species 1, R=ethyl, $R^1$=1,1-dimethylethyl, $R^2$=methyl

Under nitrogen, 9.5 ml of triethylamine was added drop-by-drop over 12 minutes to a stirred mixture of 10.0 g of ethylphosphonic dichloride, 6.14 g of 2-methyl-2-propanethiol and 50 ml of toluene at 0° C. The mixture then was stirred at 0° C. for 1 hour, at room temperature for 17 hours, then filtered. The filtrate was stripped of solvent to give S-(1,1-dimethylethyl)ethylphosphonothioic chloride (1A), as an amber liquid.

1A was dissolved in 50 ml of dry acetone, and over 10 minutes 8.4 g of a 40% aqueous solution of methylamine was added, with stirring, at 50° C. The resulting mixture was stirred at room temperature for 24 hours, then was stripped of solvent. The residue was extracted with methylene chloride, the extract was dried (Na$_2$SO$_4$) and stripped of solvent. The residue was vacuum chromatographed over silica gel, first using ethyl acetate, then ether, as eluents, to give S-(1,1-dimethylethyl) P-ethyl-N-methylphosphonamidothioate (1B) as an amber liquid.

Under nitrogen, at 5° C., 0.4 ml of pyridine, then immediately 0.4 ml of thionyl chloride, were added to a stirred solution of 0.81 g of methomyl (methyl N-(((methylamino)carbonyl)oxy)ethanimidothioate) in 2.5 ml of tetrahydrofuran (THF). The resulting mixture was stirred at room temperature for 3.75 hours, and cooled to 5° C. 0.44 ml of pyridine was added, then a solution of 0.98 g of 1B in 1 ml of THF was added, and the mixture was stirred at room temperature for 20 hours. Then the mixture was cooled to 5° C., 0.22 ml of pyridine in 1 ml of THF was added and the mixture was stirred at room temperature for 1.5 hours. The mixture was extracted with ether, the extract was washed with water, dried (Na$_2$SO$_4$) and stripped of solvent. The residue was vacuum chromatographed over silica gel, using a 1:9 v:v mixture of ether and methylene chloride as eluent. The product, an amber liquid, was held in a refrigerator overnight, whereupon it solidified. The solid was triturated with hexane to give Species 1, as a white solid, m.p.: 80°-85° C.

EXAMPLE 2

Isomeric forms of Species 1—i.e., Species 2 and 3

Under nitrogen at 5° C., 2.3 ml of pyridine, then 1.9 ml of thionyl chloride were added to a stirred solution of 4.24 g of methomyl in 25 ml of THF. The mixture was stirred at room temperature for 3 hours, then cooled to 5° C.; 2.3 ml of pyridine was added followed by a solution of 5.1 g of methomyl in 25 ml of THF. The mixture was stirred at room temperature for 18 hours, water was added, and the resulting mixture was extracted with methylene chloride. The extract was dried (Na$_2$SO$_4$) and stripped of solvent to give a crude product, which was triturated with ether and filtered to give an off-white solid, m.p.: 97°-100° C., (Species 2), identified as being predominantly (76% w) of isomer "A" of Species 1. The filtrate was vacuum chromatographed over silica gel, first using ether, then gradually replacing the ether with ethyl acetate until the final eluent was ethyl acetate, to give six fractions. The first two fractions that were obtained were combined, triturated with ether and filtered. The filtrate was dissolved in ether, washed with water, dried (Na$_2$SO$_4$) and stripped of solvent. The residue was triturated with hexane, then petroleum ether to give an off-white solid, m.p.: 71°-79° C. (Species 3), identified as being predominantly (86% w) of isomer "B" of Species 1.

EXAMPLE 3

Species 4, R=methyl, $R^1$=1,1-dimethylethyl, $R^2$=methyl

Species 4 was prepared as a white solid, m.p.: 85°-99° C., from methylphosphonic dichloride by the procedures described in Example 1 for preparing Species 1 from ethylphosphonic dichloride.

EXAMPLE 4

Species 5, R=ethyl, $R^1$=1,1-dimethylpropyl, $R^2$=methyl

Species 5 was prepared as a mixture of an amber liquid and solid, from 2-methyl-2-butanethiol, by the procedures described in Example 1 for preparing Species 1 from 2-methyl-2-propanethiol.

EXAMPLE 5

Species 6, R=ethyl, $R^1$=1-methylpropyl, $R^2$=methyl

Species 6 was prepared as a light amber liquid, from 1-methyl-1-propanethiol, by the procedures described in Example 1 for preparing Species 1 from 2-methyl-2-propanethiol.

EXAMPLES 6 AND 7

Species 7, R=ethyl, $R^1$=1-methylpropyl, $R^2$=ethyl; Species 8, R=ethyl, $R^1$=1,1-dimethyl-ethyl, $R^2$=ethyl Species 7 was prepared as a white solid, melting point not determined, and Species 8 was prepared, as an amber semi-solid, from N,P-diethylphosphonamidothioate by the procedures described in Example 1 for preparing Species 1 from P-ethyl-N-methylphosphonamidothioate.

EXAMPLE 8

Species 9, R=methyl, $R^1$=propyl, $R^2$=methyl, X=O, $R^5$=methyl, $R^6$=methyl Species 9 was prepared, as an amber liquid, from 1-propanethiol, according to the procedures described in the examples above.

EXAMPLE 9

Species 10, X=sulfur, R=methyl, $R^1$=1,1-dimethyl-ethyl, $R^2$=methyl, $R^3$=methyl, $R^5$=methyl, Y=sulfur and $R^6$=methyl, in two isomeric forms, Species 11 and 12

1,1-dimethylethyl P-ethyl-N-methylphosphonamidodithioate (9A) was prepared from ethylphosphonothioic dichloride by the procedures described in Example 1 for preparing 1B from ethylphosphonic dichloride.

9A was treated according to the procedures described in Example 2 for producing a crude product from 1B. The crude product resulting from the treatment of 9A was triturated with petroleum ether and filtered. The solid was Species 10, a white solid, m.p.: 92°-103° C. identified as a mixture of Isomers "A" and "B". A part of Species 10 was vacuum chromatographed over silica gel twice, using a 20:80 v:v mixture of hexane and ether, then a 30:70 v:v mixture of hexane and ether as eluents, to give two products, Species 11, a white solid, m.p.: 114°-117° C., identified as Isomer "A" and Species 12, a white solid, m.p.: 111°-114.5° C., identified as Isomer "B".

The compounds of the invention have been found to be toxic with respect to invertebrate pests, by which is means insects of the class Insecta and related classes of arthropods, such as the acarids (e.g., mites), ticks, spiders, wood lice and the like. It has been found that some of the compounds control insects in soil, as well as insects attacking the above-ground portions of plants. Furthermore, it has been found that compounds of the invention act systemically—that is, when applied to the plant, a compound of the invention penetrates into the cells and vascular system of the plant and is translocated therein and thereby disseminated throughout the plant without injury to the plant, yet effectively kills insects that chew upon tissues of the plant or suck juices from the plant.

For application, a compound of the invention ordinarily is applied most effectively by formulating it with a suitable inert carrier or surface-active agent, or both. The invention, therefore, also includes compositions suitable for combatting pests, such compositions comprising an inert carrier or surface-active agent, or both, and as active ingredient at least one compound of the invention. The invention also provides a method of combatting pests at a locus, which comprises applying to that locus a compound of the invention or a pesticidal composition according to the invention.

The term "carrier" as used herein means an inert solid or liquid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides— i.e., horticulturally acceptable adjuvants—are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum slicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable liquid carriers are water, alcohols such as isopropyl alcohol and glycols; ketones such as acetone, methyl ethyl ketone, methyl isobutyl ketone and cyclohexanone; ethers such as cellosolves; aromatic hydrocarbons such as benzene, toluene and xylene; petroleum fractions such as kerosene, light mineral oils; chlorinated hydrocarbons such as carbon tetrachloride, perchloroethylene and trichloromethane. Also suitable are liquefied, normally vaporous and gaseous compounds. Mixtures of different liquids are often suitable.

The surface-active agent may be an emulsifying agent or a dispersing agent or a wetting agent; it may be non-ionic or ionic. Any of the surface-active agents usually applied in formulating herbicides or insecticides may be used. Examples of suitable surface-active agents are the sodium and calcium salts of ppolyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25-75% by weight of active compound and usually contain, in addition to the solid carrier, 3-10% by weight of a dispersing agent, 2-15% of a surface-active agent and, where necessary, 0-10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5-10% by weight of the active compound. Granules are usually prepared to have a size between 10 and 100

BS mesh (1.676–0.152 mm), and may be manufactured by agglomeration or impregnation techniques. Generally, granules will contain 0.5–25% by weight of the active compound, 0–1% by weight of additives such as stabilizers, slow release modifiers and binding agents. Emsulifiable concentrates usually contain, in addition to the solvent and, when necessary, cosolvent, 10–50% weight per volume of the active compound, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight of the active compound, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Of particular interest in current practice are the water-dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulations contain 90% or more by weight of finely divided active material, 3–7% by weight of a blend of surfactants, which act as wetting, dispersing, suspending and binding agents, and 1–3% by weight of a finely divided carrier, which acts as a resuspending agent.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have thick, mayonnaise-like consistency.

It is evident from the foregoing that this invention contemplates compositions containing as little as about 0.0001% by weight to as much as about 95% by weight of a compound of the invention as the active ingredient.

The compositions of the invention may also contain other ingredients, for example, other compounds possessing pesticidal, especially insecticidal, acaricidal or fungicidal properties, as are appropriate to the intended purpose.

The method of applying a compound of the invention to control pests comprises applying the compound, ordinarily in a composition of one of the aforementioned types, to a locus or area to be protected from the insects, such as the foliage and/or the fruit of plants. The compound, of course, is applied in an amount sufficient to effect the desired action. This dosage is dependent upon many factors, including the carrier employed, the method and conditions of the application, whether the formulation is present at the locus in the form of an aerosol, or as a film, or as discrete particles, the thickness of film or size of particles, and the like. Proper consideration and resolution of these factors to provide the necessary dosage of the active compound at the locus to be protected are within the skill of those versed in the art. In general, however, the effective dosage of the compound of the invention at the locus to be protected—i.e., the dosage which the insect contacts—is of the order of 0.001 to 0.5% based on the total weight of the formulation, though under some circumstances the effective concentration will be as little as 0.0001% or as much as 2%, on the same basis.

Activity of compounds of the invention with respect to insect and acarine pests was determined using standardized test methods to measure the toxicity of the compounds as follows:

I. Houseflies (*Musca domestica* (Linne)) were tested by placing 50 4- to 5-day old adult houseflies into a spray cage and spraying with 0.6 ml of a solution of test compound. After spraying, the flies were observed to ascertain any knockdown effect, and then were anesthetized with $CO_2$ and transferred to a recovery cage containing a milk pad for food. The cages were held for 18–20 hours after which mortality counts were made. Both dead and moribund flies were counted. The test were conducted employing several different dosage rates for each test compound.

II. Pea aphides (*Acyrthosiphon pisum* (Harris)) were tested by placing about 100 aphids of all ages on broad bean plants. The plants were sprayed with dilutions of an acetone solution of the test compound in water containing an emulsifier and held in containers under laboratory conditions for 18 to 20 hours, at which time the living aphids in the containers were counted. The tests were conducted employing several different dosage rates for each test compound.

III. Adult female two-spotted spider mites (*Tetranychus urticae* (Koch)) were tested by placing 50–75 mites on the bottom side of leaves of pinto bean plants. The leaves were sprayed with dilutions of an acetone solution of the test compound in water containing an emulsifier and kept under laboratory conditions for about 20 hours, at which time mortality counts were made. The tests were conducted employing several different dosage rates for each compound.

IV. Third instar corn earworm larvae (*Heliothis zea* (Boddie)) were tested by spraying broad bean plants with dilutions of an acetone solution of the test compound in water containing an emulsifier. Immediately after spraying, 5 larvae were transferred to the plant and held for 44–46 hours, at which time the dead and moribund larvae were counted. The tests were conducted employing several different dosage rates for each test compound.

In each set of tests, identical tests were conducted using parathion as a standard for comparison.

In each instance, the toxicity of the test compound was compared to that of a standard pesticide, parathion, the relative toxicity of the test compound then being expressed in terms of the relationship between the amount of the test compound and the amount of the standard pesticide required to produce the same percentage (50%) of mortality in the test insects. By assigning the standard pesticide an arbitrary rating of 100, the toxicity of the test compound was expressed in terms of the Toxicity Index, which compares the toxicity of the test compound of the invention with that of the standard pesticide. That is to say, a test compound having a Toxicity Index of 50 would be half as active, while one having a Toxicity Index of 200 wuld be twice as active, as the standard pesticide. The results are set forth in Table I.

TABLE I

| Species | Toxicity Index | | | |
|---|---|---|---|---|
| | House-fly | Pea Aphid | Corn Earworm | Spider Mite |
| 1 | 20 | 10 | 395 | 555 |
| 2 | 10 | 25 | 200 | 670 |
| 3 | 10 | 30 | 160 | 640 |
| 4 | 15 | 5 | 90 | 720 |
| 5 | 20 | 15 | 380 | 320 |
| 6 | 10 | 40 | 270 | 100 |
| 7 | 15 | 15 | 330 | 110 |
| 8 | 10 | 10 | 300 | 500 |
| 9 | 20 | 10 | 210 | 480 |
| 10 | 15 | 5 | 225 | 155 |
| 11 | 11 | 0 | 65 | 0 |
| 12 | 10 | 0 | 210 | 0 |

It is to be noted that Species 11 and 12 are isomeric forms, Species 10 being a mixture of those forms, and that the activity levels and spectra of the isomeric forms differ from that of the mixture. These results appear to reflect an example of biochemical interactions between isomers of differing activity.

In one embodiment of the invention, compounds of Formula I are used to control larvae of soil-dwelling insects that attack plants growing in the soil, the method for control of such insects comprising providing in the soil in which the plants are growing, or are to be grown, an insecticidally effective dosage of a compound of Formula I. For the same reason, the invention also embodies a method for protecting a plant from attack by insects dwelling in the soil in which the plant is growing, that method comprising providing in the soil in which the plant is growing or in which it is to be grown, an insecticidally effective dosage of a compound of Formula I.

Compounds of the invention may be used to control a variety of soil-dwelling insects, such as species of Diabrotica, for example, *Diabrotica virgifera virgifera, D. longicornis barberi* and *D. undecimpunctata howardi*, the western, northern and southern corn rootworms, respectively; species of Agrotis, Crymodes, Amathes, Euxoa, Peridroma, Lacinipolia, Nephelodes, Actebia, Feltia, Loxagrotis (cutworms), Agriotes, Limonium, Horistonotus, Ctenicera, Conoderus (wireworms), and the like, some of the bettern known species being: *Agrotis ipsilon* (black cutworm), Agriotes mancus (wheat wireworm) and the three Diabrotica species mentioned above.

For use as soil insecticides, the compound of Formula I suitably is applied to the soil at a rate of from about 0.01 to about 10 kilograms per hectare. Good control of soil inhabiting insects or their lavae is obtained at rates of from about 0.1 to about 5 kilograms per hectare and especially from about 0.5 to about 4 kilograms per hectare. The compound of Formula I can conveniently be formulated for use as a granule or powder containing a solid diluent, impregnated with the compound. Such formulations usually contain from about 1 to about 50% by weight of the compound. More effective control results when the formulation is physically lightly mixed with the topsoil. The mixing is preceded or immediately followed by planting seeds which germinate into plants. The compound of Formula I can be applied as a drench—that is, as a solution or dispersion of the compound in a non-phytotoxic solvent or liquid diluent, suitably water. Such drenches can be prepared by diluting with water a concentrate containing the compound of Formula I, an emulsifying agent, and preferably an organic solvent, such as toluene. The compound of Formula I can be applied by band, furrow or side-dress techniques, and may be incorporated or not.

Activity of compounds of Formula I with respect to soil-dwelling insect pests was determined as follows:

Corn Rootworm test

The test chemical was dissolved in acetone and the solution was mixed with water containing 0.055% Atlox 1045A. The amounts of test compound and water were so chosen as to provide 500 grams of a soil mixture containing 9% by weight of water and three parts per million (ppm) by weight of the test compound. The materials were thoroughly mixed to give a homogeneous mixture.

Sixty grams of the soil mixture was added to a 4 ounce wide-mouthed jar (until it was about half full). Two sweet corn seeds, which had been surface sterilized in 0.2% sodium hypochlorite solution for fifteen minutes and rinsed with water, were pressed into the soil near the perimeter of the jar. A small cavity of about 2.5 cubic centimeters was opened in the surface of the soil and 20 *Diabrotica undecimpunctata undecimpunctata* Mannerheim (western spotted cucumber beetle) eggs were placed in the cavity. The eggs were immediately covered with fine-seived Zonolite or vermiculite and the covering material was wetted with about 1.5 cubic centimeters of water. The jar was then capped with a lid into which two 2.5-millimeter holes had been drilled for ventilation. The jars were held under lamps at 27° C. The eggs were generally two to four days old. Two replicates were conducted. The remainder of the soil was held in a sealed container at room temperature. Eight days later, the contents of the jar were examined for the presence of live larvae, the number thereof was recorded and the corn roots were examined for feeding damage. Compounds showing control at 1 ppm or lower rate in the first week were evaluated at subsequent weeks—i.e., at 2, 4 and 8 weeks—so long as activity justified further testing. Each of these tests were conducted in sequence, as described above, by using samples of the soil mixture from the sealed container that had been held for the appropriate length of time. Each test period was designated by the age of the soil mixture at the beginning of the test, with the results being ascertained one week later—i.e., the test period designated as zero employed freshly prepared soil mix, results read one week later, the test period designated as two weeks employed two-week-old mix, results read one week later, etc.

The results of the tests were reported as $LC_{50}$ dosages, based on the amount of test chemical in the soil.

The results are set out in Table II.

TABLE II

| Species | $LC^{50}$ dosage (ppm) at time indicated | | |
|---|---|---|---|
| | 0 Weeks | 4 Weeks | 8 Weeks |
| 1 | 0.6 | 1.5 | — |
| 2 | <1 | 1.8 | — |
| 3 | <1 | 1.0 | — |
| 4 | <1 | <1 | — |
| 5 | <1 | 0.83 | — |
| 6 | <1 | <1 | <1 |
| 7 | <1 | 1.0 | — |
| 8 | >1 | — | — |
| 9 | >1 | — | — |
| 10 | 1.1 | >1 | — |
| 11 | <1 | 0.94 | 1.8 |

TABLE II-continued

| | LC$^{50}$ dosage (ppm) at time indicated | | |
|---|---|---|---|
| Species | 0 Weeks | 4 Weeks | 8 Weeks |
| 12 | >1 | — | — |

Systemic Activity Tests

Systemic activity of compounds of Formula I was determined as follows:

Mite Tests

The roots of pinto bean plants (*Phaseolus vulgaris*) in the primary leaf stage were placed in a flask containing water plus the test chemical. The stem of the plant was wrapped with non-absorbent cotton fitted snugly into the neck of the flask, to prevent possible fumigant action by the test chemical. Then the plant was infested with 50–100 adult female two-spotted spider mites, held for 48 hours at 85° F., and 50% relative humidity when mortality in the mites was determined visually. A series of different dosages of the test compound in the water were used, and the LC$_{50}$ dosage (the dosage in parts per million by weight of the test chemical in the water required to effect fifty percent kill of the mites) was determined. The results are set forth in Table III.

TABLE III

| Species | LC$_{50}$ Dosage (ppm) |
|---|---|
| 1 | 2.5 |

Aphid Tests

Broad bean plants in the 6 to 8 leaf stage were removed from pots and their roots were washed free of soil. Each was placed in a flask containing 100 ml of a water solution of the test compound. The plant stems were wrapped with non-absorbent cotton which fit snugly into the neck of the flask to prevent possible fumigant action by the test compound. The flask was positioned under a wooden stage with the stem of the plant extending up through a slot in the stage. A 6"×6" square of paper was placed flat on the stage around the stem of the plant. A plastic ring 5 inches in diameter and 2 inches high, coated on the inside with petroleum jelly, was placed around the plant to prevent the aphids from escaping. 50 to 100 aphids were placed within each ring. Then the plant was held for 48 hours at 85° F., and 50% relative humidity when mortality in the mites was determined visually. A series of different dosages of the test compound in the water were used, and the LC$_{50}$ dosage (the dosage in parts per million by weight of the test chemical in the water required to effect fifty percent kill of the aphids) was determined. The results are set forth in Table IV.

TABLE IV

| Species | LC$_{50}$ Dosage (ppm) |
|---|---|
| 7 | 1.5 |

What is claimed is:

1. A compound of the formula $$\begin{array}{c} \quad\quad\quad X \quad R^2 \quad\nearrow\!\!\!\!\uparrow\!\!\!\!\nwarrow O \quad R^3 \quad O \\ \quad\quad\quad \| \quad | \quad | \quad | \quad \| \\ R-P-N-S-N-C-O-N=R^4 \\ \quad\quad | \\ \quad\quad S-R^1 \end{array} \quad (I)$$

wherein R and R$^1$ each is alkyl or alkenyl of up to six carbon atoms, phenyl or benzyl, R$^2$ is alkyl, alkenyl or alkynyl of up to six carbon atoms, or such alkyl substituted by phenyl; phenyl or phenyl substituted by one to three substituents selected from alkyl of one to six carbon atoms and halogen; R$^3$ is methyl; X is oxygen or sulfur, and R$^4$ is

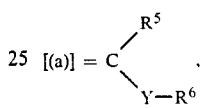

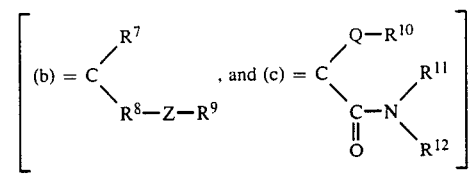

wherein R$^5$ is alkyl of one of five carbon atoms, Y is oxygen or sulfur and R$^6$ is alkyl of one to six carbon atoms.

2. A compound according to claim 1 wherein each of R$^2$, R$^3$, R$^5$ and R$^6$ is methyl and Y is sulfur.

3. A compound according to claim 2 wherein R is ethyl, X is oxygen and R$^1$ is 1,1-dimethylethyl.

4. A method for controlling insects and/or acarids at a locus that comprises subjecting them to an effective dosage of a compound of claim 1.

5. A method for controlling insects and/or acarids at a locus that comprises subjecting them to an effective dosage of a compound of claim 2.

6. A composition adapted to the control of insects and acarids that comprises an effective amount of a compound of claim 1 together with a carrier and a surface-active agent.

7. A composition adapted to the control of insects and acarids that comprises an effective amount of a compound of claim 2 together with a carrier and a surface-active agent.

* * * * *

UNITED STATES PATENT AND TRADEMARK OFFICE
CERTIFICATE OF CORRECTION

PATENT NO. : 4,686,209

DATED : August 11, 1987

INVENTOR(S) : Mohamed A. H. Fahmy

It is certified that error appears in the above—identified patent and that said Letters Patent is hereby corrected as shown below:

In Claim 1, column 14, lines 25 to 35, delete the bracketed material.

Signed and Sealed this

Twenty-second Day of March, 1988

Attest:

Attesting Officer

DONALD J. QUIGG

Commissioner of Patents and Trademarks